(12) United States Patent
Ahlnäs et al.

(10) Patent No.: US 8,361,210 B2
(45) Date of Patent: *Jan. 29, 2013

(54) METHOD FOR TREATING WOOD

(75) Inventors: Thomas Ahlnäs, Kotka (FI); Jari-Jukka Kukkonen, Oulu (FI)

(73) Assignee: Oy Granula AB Ltd., Kotka (FI)

( * ) Notice: Subject to any disclaimer, the term of this patent is extended or adjusted under 35 U.S.C. 154(b) by 144 days.

This patent is subject to a terminal disclaimer.

(21) Appl. No.: 12/900,773

(22) Filed: Oct. 8, 2010

(65) Prior Publication Data

US 2011/0088590 A1    Apr. 21, 2011

Related U.S. Application Data

(63) Continuation-in-part of application No. 11/794,669, filed as application No. PCT/FI2006/000007 on Jan. 4, 2006, now Pat. No. 7,812,055.

(30) Foreign Application Priority Data

Jan. 4, 2005    (FI) .................................. 20050003

(51) Int. Cl.
C09D 5/18    (2006.01)
A01N 3/00    (2006.01)
(52) U.S. Cl. ...................... 106/18.31; 106/18.32; 427/4
(58) Field of Classification Search .................. 514/553, 514/557, 578; 106/18.31, 18.32; 427/4
See application file for complete search history.

(56) References Cited

U.S. PATENT DOCUMENTS

| 2,291,634 | A | 1/1940 | Katzman et al. |
| 2,311,910 | A | 2/1943 | Straughn |
| 6,087,303 | A | 7/2000 | Walker |
| 6,352,583 | B1 | 3/2002 | Goettsche et al. |
| 7,812,055 | B2 * | 10/2010 | Ahlnas ........................ 514/553 |
| 2005/0124723 | A1 | 6/2005 | Fritschi et al. |

FOREIGN PATENT DOCUMENTS

| EP | 0 039 538 A1 | 11/1981 |
| EP | 0 238 051 A1 | 7/2001 |
| FI | 103704 B | 8/1999 |
| FI | 110661 B | 3/2003 |

* cited by examiner

*Primary Examiner* — Raymond Henley, III
(74) *Attorney, Agent, or Firm* — Young & Thompson

(57) ABSTRACT

Described is a method for treating wood, in which the wood is brought into contact with a mixture of liquid or water-soluble organic ammonium carboxylate and an active ingredient which repels invertebrates, characterized in that the organic ammonium carboxylate has the formula (1):

$$[NR^1R^2R^3R^4]^+{}_n[R^5(COO)_n]^{-n} \qquad (1),$$

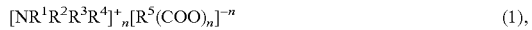

in which $R^1$, $R^2$ and $R^3$ are selected from hydrogen, substituted and unsubstituted alkyls containing 1-6 carbon atoms, $R^4$ is a substituted or unsubstituted alkyl containing 1-6 carbon atoms, $R^5$ is hydrogen, a substituted or unsubstituted hydrocarbon containing 1-6 carbon atoms and n is an integral 1-6 and whereby wood-preservative active ingredient contains a chelating agent which repels invertebrate, which chelating agent is selected from an aminopolycarboxylic acid or a salt thereof, a hydroxy acid or a salt thereof or a phosphonate or a salt thereof or a mixture of chelating agents which belong to two of more groups thereof.

57 Claims, 6 Drawing Sheets

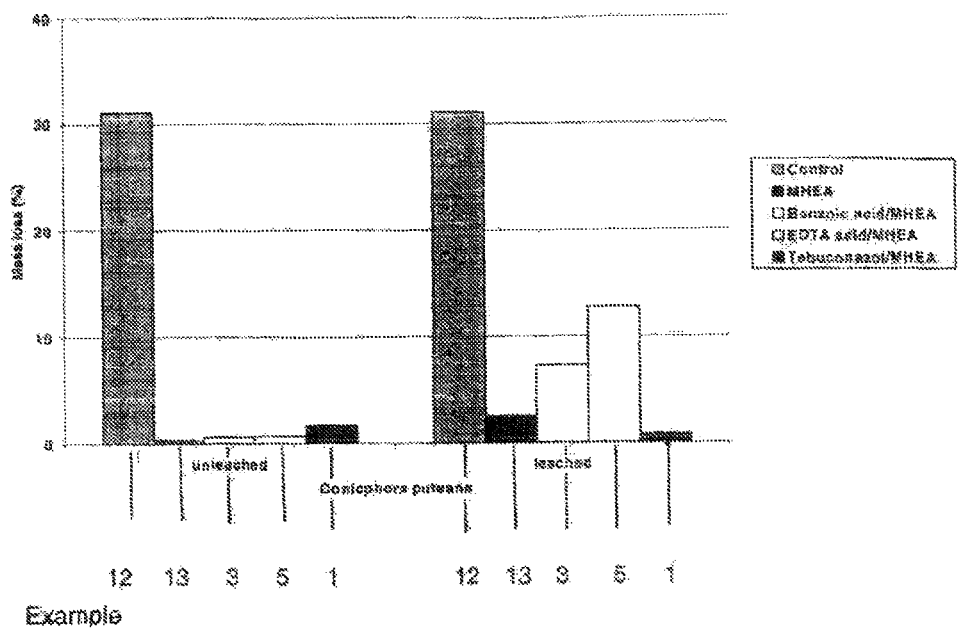
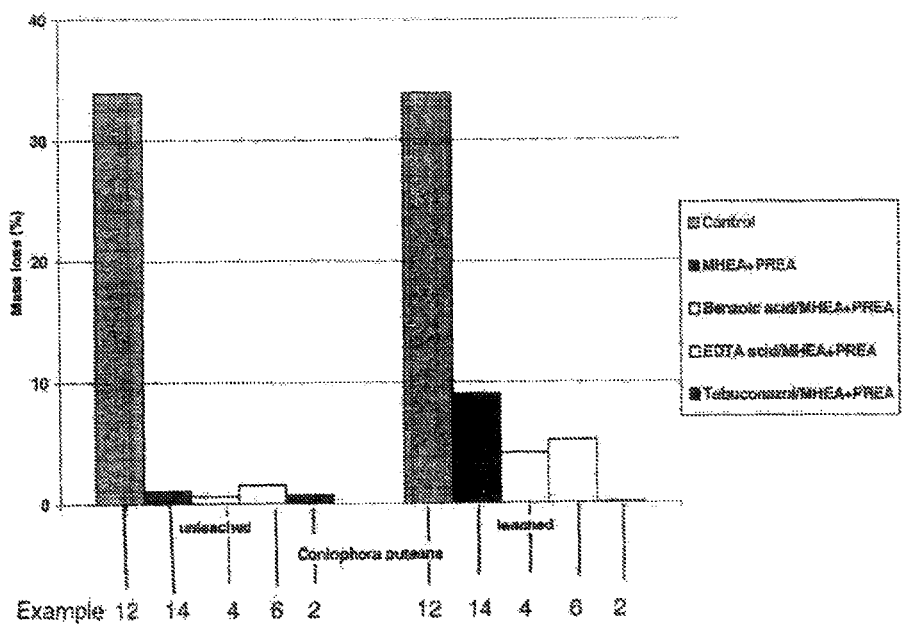
Figure 1. Anti-decay effect of commercial and new active ingredients when mixed in MHEA and MHEA+PREA carriers.

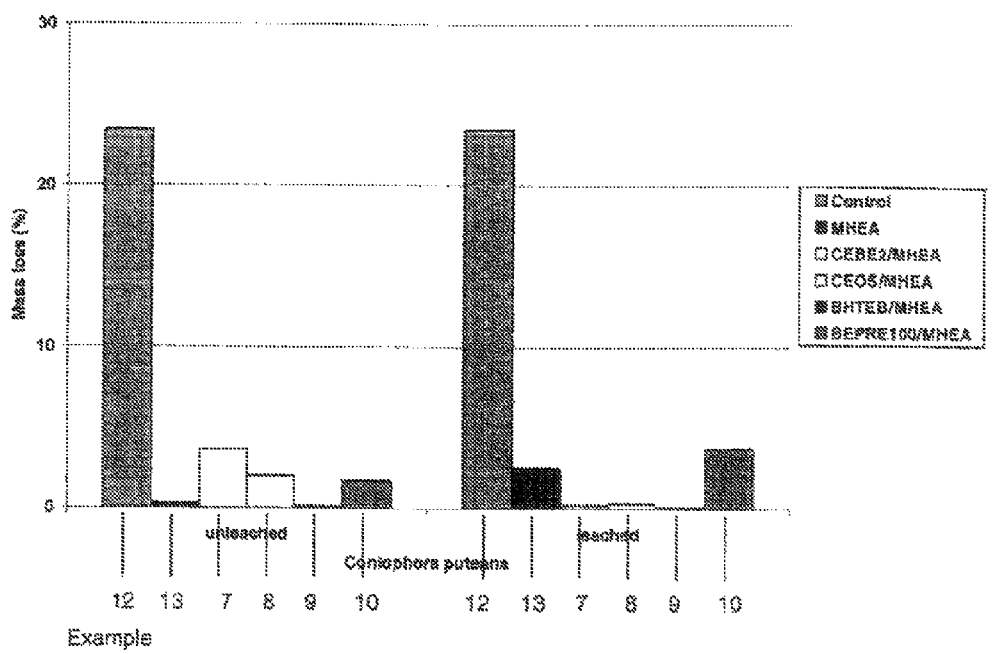
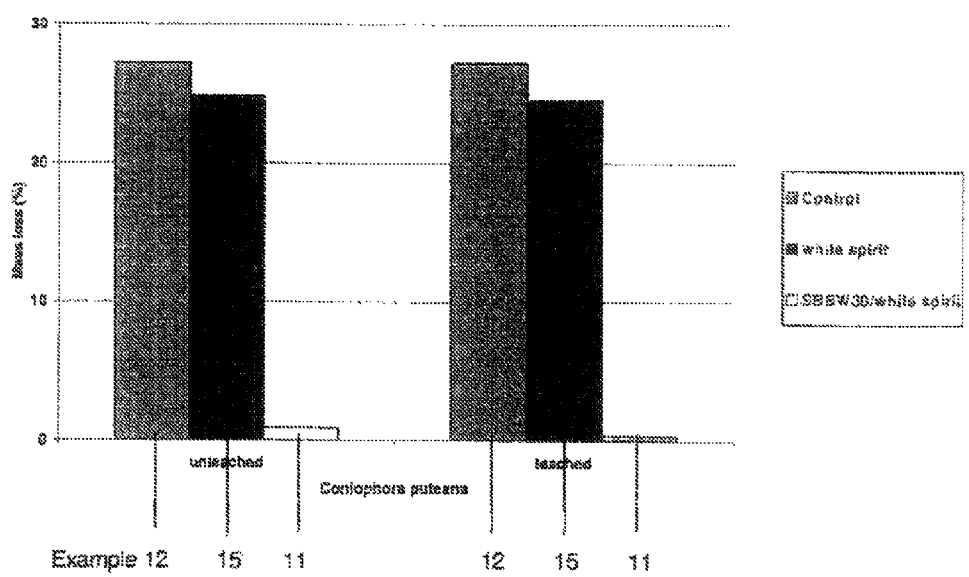
Figure 2. Anti-decay effect of mixtures of active ingredient and carrier prepared by the company Granula Oy.

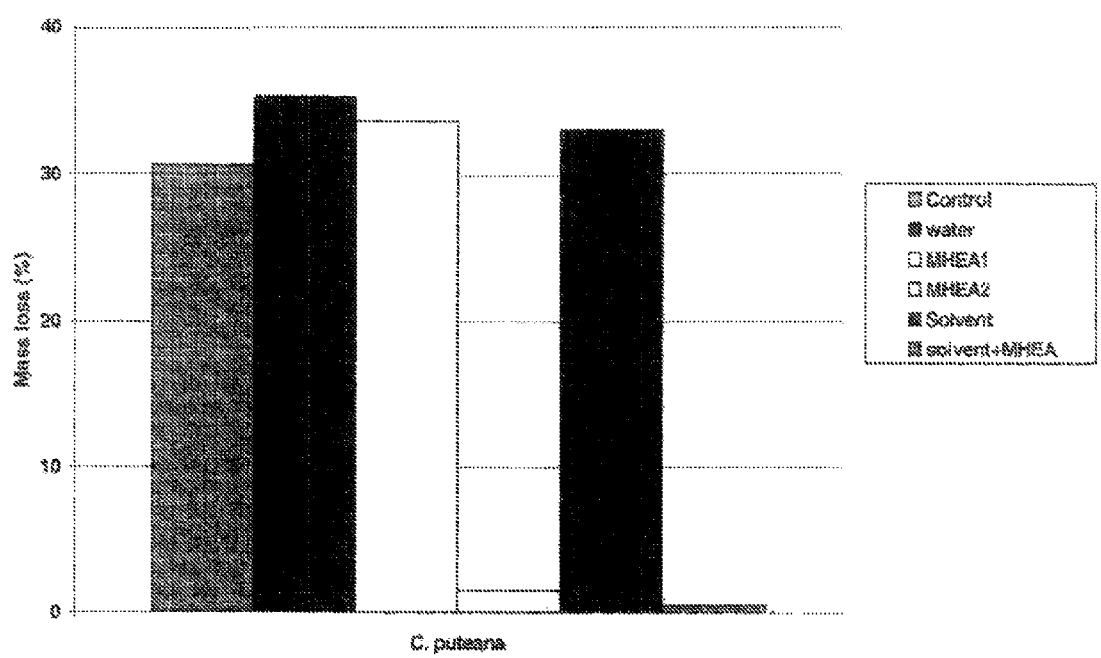
Figure 3. Effect of the extraction schedules on the anti-decay properties of wood material.

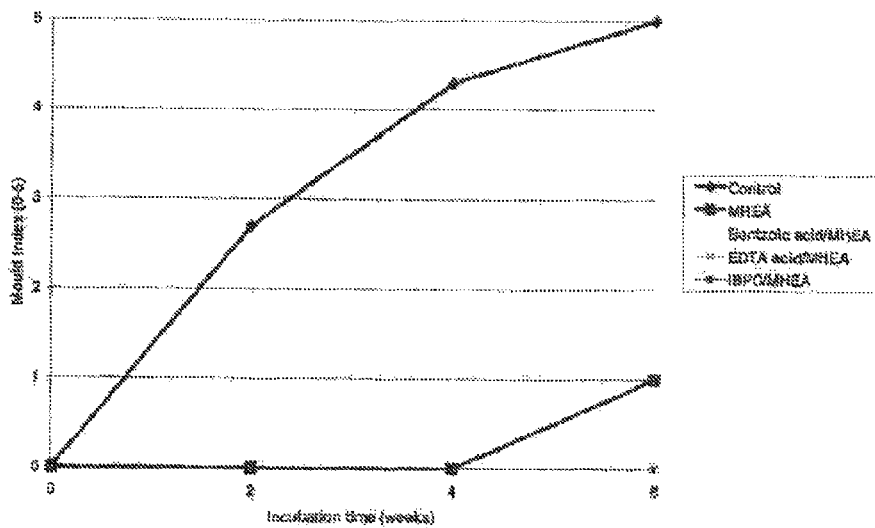
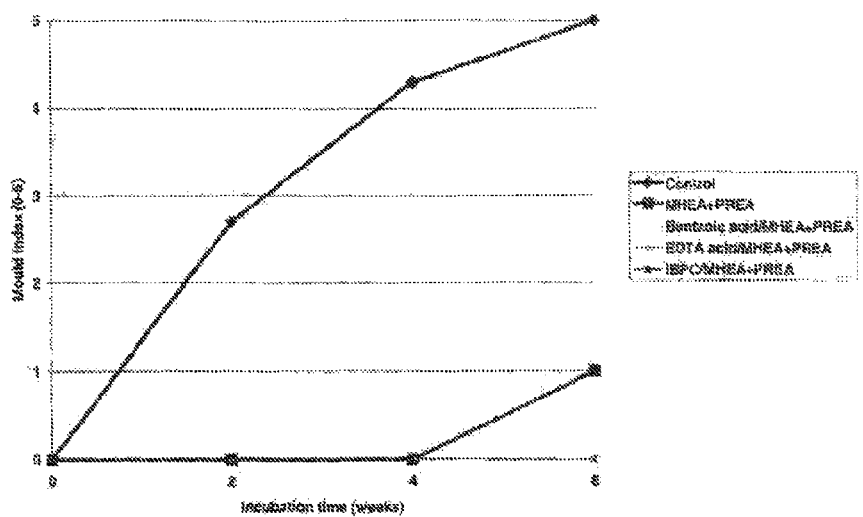
Figure 4. Anti-mildew effect of commercial and new active ingredients when mixed in MHEA and MHEA+PREA carriers.

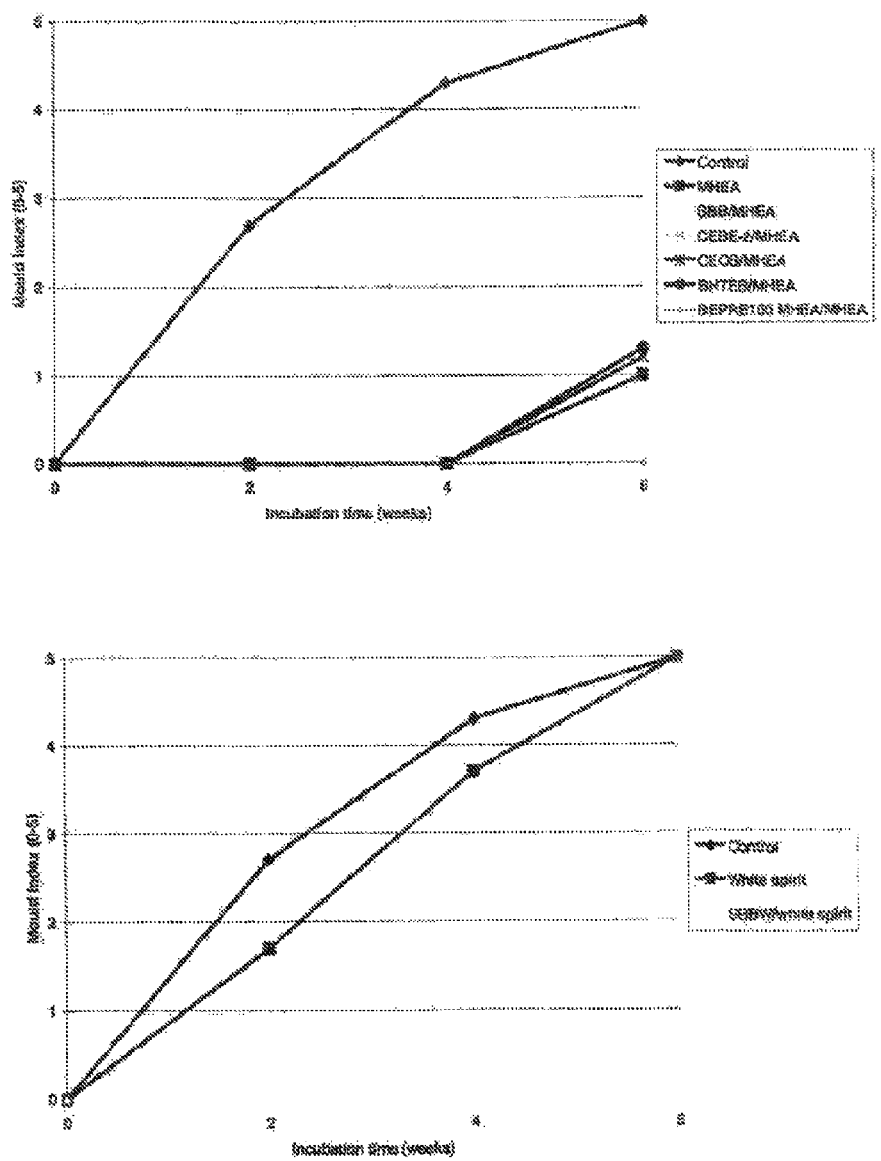
Figure 5. Anti-mildew effect of the mixtures of active ingredient and carrier produced by the company Granula Oy.

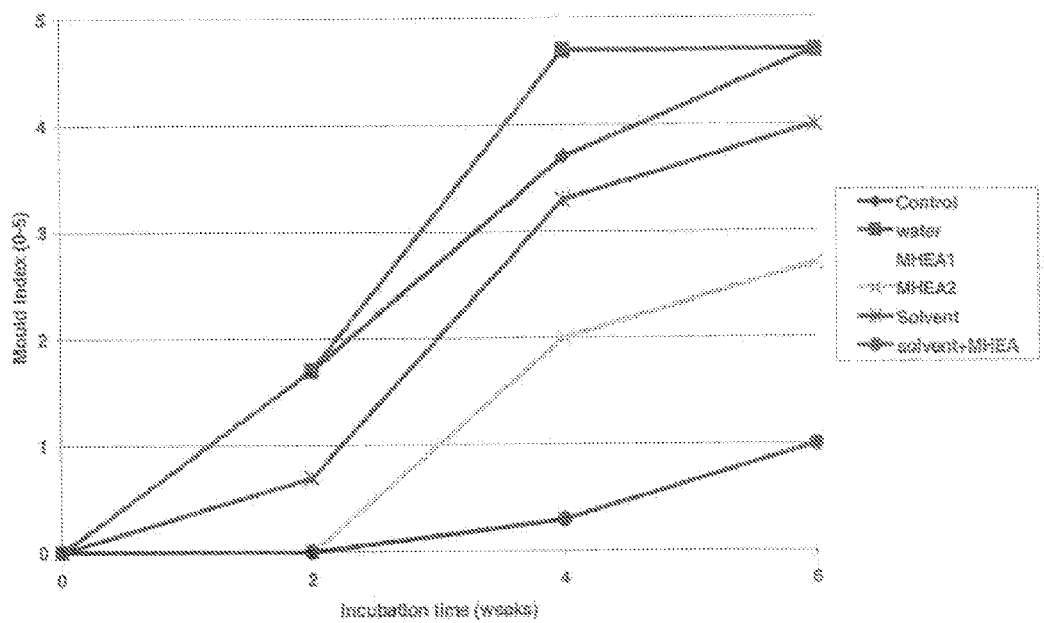
Figure 6. Effect of the extraction schedules on the anti-decay properties of wood material.

METHOD FOR TREATING WOOD

CROSS REFERENCE TO RELATED APPLICATIONS

This application is a Continuation-in-Part of application Ser. No. 11/794,669 filed on Aug. 8, 2007, now U.S. Pat. No. 7,812,055; which is the 35 U.S.C. 371 national stage of International application PCT/FI2006/000007 filed on Jan. 4, 2006; which claimed priority to Finnish Application No. 20050003 filed on Jan. 4, 2005.

FIELD OF THE INVENTION

The invention relates to a method for treating wood, in which wood is contacted with liquid or water-soluble organic ammonium carboxylate and an agent controlling invertebrates. The invention also relates to a wood preservative composition containing organic ammonium carboxylate and an agent controlling invertebrates. Additionally invention relates to the composition containing organic ammonium carboxylate and an agent controlling invertebrates.

BACKGROUND OF THE INVENTION

WO patent specification 95/27600, example 2, discloses a wood preservative comprising, in addition to zinc and copper acetate, ammonium acetate and preferably a quaternary ammonium compound, such as didecyl dimethyl ammonium chloride.

U.S. Pat. No. 4,929,454 (column 2, line 60-column 3, line 6) discloses a method for preparing wood by impregnating wood with zinc, copper and a quaternary ammonium compound, which may consist of tertiary $C8$-$C_{20}$ alkyl ammonium salt of fatty acid. However, the use of copper and zinc may cause environmental and corrosive problems.

EP patent specification 1 114 704 A2 discloses a wood preservative without copper and zinc, which contains water-soluble organic ammonium carboxylate. The ammonium ion of this quaternary ammonium carboxylate comprises a $C_1$-$C_{20}$ alkyl group or an aryl substituted alkyl group and at least one, preferably two alkyl groups containing 8-20 carbon atoms, cf. paragraph [0051] of the specification. The carboxylate may be e.g. acetate, cf. paragraph [0224], or propionate, cf. paragraph [0219]. In addition to a microbicide property, the preservatives containing quaternary ammonium carboxylates of the reference have enhanced retention, and they can even be used without metal stabilisers, such as combinations of arsene, chromium, copper and zinc, cf. paragraph [0032] of the reference.

However, the ammonium carboxylates of these references involve the problem of not being absorbed into wood in adequate amounts, or of having poor retention in wood.

There are several widely known agents which can be used for controlling insects such as termites:

Disodium Octaborate Tetrahydrate (DOT) is used against fungi, insects and termites. DOT maximizes the solubility, the rate of dissolution and the boric oxide content to give a borate active ingredient far superior to traditional boric acid or borax. At the levels used in professional applications, it prevents pest infestation by inhibiting pest metabolism on a cellular basis. The tetrahydroxyborate anion forms a chelate complex with the cis-adjacent hydroxyl groups in the ribose sugar of nicotinamide adenine dinucleotide (NAD), with the cationic nitrogen of the nicotinamide moiety providing electrostatic stabilization of the chelate. In this configuration, NAD and NADP cannot be used by the dehydrogenase enzymes of glycolysis, the pentose phosphate pathway or the tricarboxylic acid pathway, and so the cellular energy generating mechanisms, including adenosine triphosphate production, are shut down.

Permethrin is one of many synthetic pyrethroids. Permethrin is a neurotoxin and it is used against a variety of pests, on nut, fruit, vegetable, cotton, ornamental, mushroom, potato, and cereal crops. It is used in greenhouses, home gardens, and for termite control. It also controls animal ectoparasites, biting flies, and cockroaches. Permethrin kills insects by strongly exciting their nervous systems. Rather than sending a single impulse in response to a stimulus, permethrin-exposed nerves send a train of impulses, similar to that of the organochlorine insecticide DDT. Membrane ATPases are a target of the neurotoxic effect of pyrethroid compounds which could explain the effect on the immune apparatus. Permethrin is toxic to honey bees and other beneficial insects, fish, aquatic insects, crayfish, and shrimp. For many species, concentrations of less than one part per billion are lethal. Permethrin causes deformities and other developmental problems in tadpoles, and reduces the number of oxygen-carrying cells in the blood of birds.

The above mentioned agents used widely for insect control are relatively harmful for beneficial insects which will limit severely their use for example in wood treating; if these agents are impregnated into wood their concentration should be kept considerably low.

There are also several prior art methods for preparing wood, in which wood is impregnated with copper compounds, a reaction mixture or a complex of ammonium carboxylate and copper compounds (e.g. U.S. Pat. No. 6,352,583 and EP 238 051). Such wood preservatives have the drawback of using toxic copper compounds and/or of having poor retention in wood and/or poor absorption into wood.

SUMMARY OF THE INVENTION

The purpose of the invention is thus to provide a method and a composition for preparing wood, in which the composition is both well absorbed and has good retention.

Another objective of the invention is to provide a method for preparing wood, which does not require the use of arsenic, chromium, copper or zinc compounds as stabilisers.

Yet another objective of the invention is to provide a method and a composition for protecting wood against invertebrates specifically against insects and yet more specifically against ants and termites which composition is intoxic against harmless invertebrates or insects so that it can be used in sufficiently large amounts when impregnated in wood material.

The objectives mentioned above have now been achieved with a new method for preparing wood with liquid or water-soluble organic ammonium carboxylate of the type above, in combination with a wood preservative active ingredient containing invertebrate repelling chelating agent. The active ingredient is preferably a mixture or a reaction product of an organic active ingredient salt and an organic active ingredient acid.

The organic ammonium carboxylate has the formula (1):

$$[NR^1R^2R^3R^4]^+{}_n[R^5(COO)_n]^{-n} \qquad (1)$$

in which $R^1$, $R^2$ and $R^3$ have been selected from the group comprising hydrogen, substituted alkyls having 1-6 carbon atoms and unsubstituted alkyls having 1-6 carbon atoms, $R^4$ is a substituted alkyl having 1-6 carbon atoms or an unsubstituted alkyl having 1-6 carbon atoms, $R^5$ is hydrogen, a substituted hydrocarbyl having 1-6 carbon atoms or an unsubstituted hydrocarbyl having 1-6 carbon atoms, and n is an integer between 1-6. Such an ammonium carboxylate is readily absorbed in very large amounts into wood and is subsequently retained in the wood. Wood preservative active ingredient contains a chelating agent, that repels invertebrate, which chelating agent is selected from the group comprising an aminopolycarboxylic acid or salt thereof, a hydroxy acid or a salt thereof, or a phosphonate (i.e. organic phosphonate i.e. organophosphate) or a mixture of chelating agents which belong to two of more groups thereof.

Wood preparation involves contacting the wood with another substance. Organic ammonium carboxylate stands for a salt or a complex formed of an ammonium cation and a carboxylic anion. Hence one or more ammonium ions of the salt or complex may be primary ($RNH_3^+$), secondary ($R_2NH_2^+$), tertiary ($R_3NH^+$) or quaternary ($R_4N^+$). The carboxylate ion of the salt or complex may be monovalent ($RCOO^-$) or polyvalent ($R(COO^-)_{n>1}$), and in that case it may also comprise unneutralised carboxyl groups (—COOH). In the latter case, $R^5$ is defined as being substituted with carboxyl.

Solution comprising ammonium carboxylate and wood preservative is intended against invertebrates, which stands here mainly insects such as termites and ants. However said solution may be also useful against worms and snails. Additionally some forms of composition according to invention may be useful against vertebrate pests.

FI patent specifications 103704 B and 110661 B disclose methods for fodder preservation by means of ammonium carboxylates having a structure similar to that of the compounds of formula (1). Nonetheless, the problems occurring in fodder preservation are different from those relating to the present wood preparation method, because fodders are not prepared with chelating agents and toxic metals such as copper, and impregnation of fodder with preservatives does not involve the same problems as impregnating wood with wood preservatives. The objective of fodder preservation is lactic acid fermentation together with prevention of harmful microbial, yeast and mildew growth.

Group $R^5$ in formula (1) is preferably hydrogen, substituted alkyl containing 1-6 carbon atoms or unsubstituted alkyl containing 1-6 carbon atoms, more advantageously hydrogen, substituted alkyl containing 1-4 carbon atoms or unsubstituted alkyl containing 1-4 carbon atoms. The terms "substituted" and "unsubstituted" refer basically to groups containing heteroatoms (e.g. —OH, —$NH_2$, —COOH).

Since the group $R^5$ is associated with a carboxylate group, the ammonium carboxylate of formula (1) is preferably based on a lower organic carboxylic acid and it can be prepared from such an acid or its salt. Lower organic acids include lower fatty acids such as formic acid, acetic acid, propionic acid, n- and i-butyric acid, and n- and i-pentanic acid. Useful acids also include benzoic acid and oxycarboxylic acids such as glycolic acid and lactic acid. Lower dicarboxylic acids such as oxalic acid, malonic acid, succinic acid and glutaric acid are also applicable.

Group $R^5$ of formula (1) is most advantageously hydrogen, methyl or ethyl. In formula (1), n is preferably 1 or 2, most advantageously 1. Consequently, the most advantageous organic ammonium carboxylate used in the method of the invention is based on lower fatty acids.

As mentioned above, the ammonium ion of formula (1) may be primary ($RNH_3^+$), secondary ($R_2NH_2^+$), tertiary ($R_3NH^+$) or quaternary ($R_4N^+$), and then R is typically a substituted or unsubstituted alkyl containing 1-6 carbon atoms. Typical ammonium ions containing unsubstituted alkyls have been formed from water-soluble amines such as methylamine (g), dimethylamine, trimethylamine, ethylamine, diethylamine, etc.

Ammonium ions containing substituted alkyls have typically been formed from water-soluble amines, whose alkyl(s) have been substituted with one or more hydroxyl groups. In formula (1), $R^1$ is preferably hydrogen and $R^2$ and $R^3$ have preferably been selected from the group comprising hydrogen and $C_1$-$C_6$-alkyls substituted with a hydroxyl group, preferably from the group comprising hydrogen and $C_1$-$C_4$-alkyls substituted with a hydroxyl group. $R^4$ is preferably a $C_1$-$C_6$-alkyl substituted with a hydroxyl group, most advantageously a $C_1$-$C_4$-alkyl substituted with a hydroxyl group.

Organic ammonium carboxylates formed of lower alkanolamines are hence particularly useful. Among lower alkanolamines we may cite monoethanolamine, diethanolamine, triethanolamine, monoisopropanolamine, di-isopropanolamine, triisopropanolamine, mono-sek-butanolamine, di-sek-butanolamine and tri-sek-butanolamine.

One important group of useful alkanolamines comprises lower alkyl alkanolamines, such as methyl ethanolamine, dimethylethanolamine, diethylethanolamine, butylethanolamine, methyldiethanolamine and ethyldiethanolamine. Additional information about useful alkanolamines can be found in the book Kirk-Othmer, Encyclopedia of Chemical Technology 3rd Ed., Vol. 1, p. 944, which is incorporated in this disclosure.

It is particularly recommendable that $R^1$ is hydrogen, $R^2$ and $R^3$ are selected from the group comprising hydrogen and ethyl substituted with a hydroxyl group, preferably from the group comprising hydrogen and 2-hydroxy ethyl, and $R^4$ is ethyl substituted with a hydroxyl group, preferably 2-hydroxy ethyl. Consequently, the ammonium carboxylate in accordance with the invention is preferably based on ordinary mono, di or triethanolamine.

In the most advantageous embodiment, the organic ammonium carboxylate of formula (I) is selected from the group comprising a salt or a complex of formic acid and monoethanolamine and a salt or a complex of propionic acid and monoethanol amine. These agents will provide maximum absorption of the substance into wood and retention in the wood. In one optional embodiment, organic ammonium carboxylate is a mixture of a salt of formic acid and monoethanolamine and a salt of propionic acid and monoethanolamine, preferably in the weight ratio 80:20-20:80.

Wood-preservative active ingredient, which is used in combination of mentioned ammonium carboxylate of formula (1), contains chelating agent, which is selected from the group comprising of an aminopolycarboxylic acid or salt thereof, a hydroxy acid or a salt thereof, or a phosphonate (i.e. organic phosphonate i.e. organophosphate) or a mixture thereof.

Chelation is the formation or presence of two or more separate bindings between a polydentate (multiple bonded) ligand and a single central atom. Usually these ligands are organic compounds, and are called chelants, chelators, chelating agents, or sequestering agents. Chelating agents are chemicals that form soluble, complex molecules with certain metal ions, inactivating the ions so that they cannot normally react with other elements or ions to produce precipitates or scale.

Preferably the chelating agent according to the invention is a chelating agent being able to bind iron and manganese ions and that contain phosphorus (P) in the molecular structure such as HEDP.

When chelating acid is a complexing agent it can be selected from the group comprising ethylenediaminetetraacetic acid (EDTA), nitrolotriacetic acid (NTA), n-hydroxyethyl-ethylenediaininetriacetic acid (HEDTA), diethylenetriaminepentaacetic acid (DTPA), ethylediamine-di-o-hydroxyphenylacetic acid (EDDHDA), diethanolglycine (DEG), ethanoldiglycine (EDG) or salt thereof or 1-hydroxyethylidene, 1,1-diphosphonic acid (HEDP), ethylenediaminetetramethylenephosphonic acid (EDTMP), diethylenetriaiminepentamethylenephosphonic acid (DTPMP) or salt thereof or a mixture thereof.

Preferably chelating agent contains phosphor. Most preferred phosphor containing chelating agents are 1-hydroxyethylidene,1,1-diphosphonic acid (HEDP), ethylenediaminetetramethylenephosphonic acid (EDTMP), diethylenetriaiminepentamethylenephosphonic acid (DTPMP) or salt thereof or a mixture thereof.

The ammonium carboxylate of formula (1) can also be contacted with wood by preparing it from its starting material in situ, in other words substantially in contact with wood. Typical starting materials then comprise hydroxide or a salt formed by an ammonium ion of formula (1), such as chloride, and an acid or salt formed by an acid ion of formula (1), e.g. sodium salt, resulting mainly in the following reaction (2):

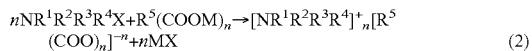

(2)

stable in which $R^1$, $R^2$, $R^3$, $R^4$, $R^5$ and n are identical to those of formula (1) and X and M are an anion respectively a cation forming a stable acid or salt. Typical anions X comprise hydroxyl and halogenides and typical cations M comprise proton and alkali and earth alkali metals.

In the practice, ammonium carboxylate of formula (1) is prepared e.g. by mixing an ammonium cation source and a carboxyl anion source in the desired molar ratio, either without a medium or by using an appropriate solvent such as water as a medium. When the starting material is an amine and an acid, they are simply mixed during gentle heating, if necessary. When the starting materials consist of salts, they are typically dissolved separately in water, and then the solutions are combined. If the salt or complex thus formed is hydrophobic, it will separate from the water phase as an unctuous or paste-like deposit or a wax-like precipitate, and it can be separated from the water phase by any known methods. When both the starting materials and the formed product are hydrophobic, the preparation can be carried out in an organic solvent instead of water.

Preliminary results indicate, that when ammonium carboxylate of formula (1) is for instance a fluid pair: ethylene amine—formic acid, it can under special circumstances react and form amide when no solvent is present. Increasing temperature favours amide formation. Nearly no esters are formed.

Raw material for the organic ammonium carboxylates of formula (1) as well as compositions and solutions obtained from these carboxylates can be got from re-use of the freezing point depressant compositions described in U.S. patent application 12/639,109 for Ahlnäs et al.

BRIEF DESCRIPTION OF THE DRAWINGS

FIG. 1 shows an anti-decay effect of commercial and new active ingredients when mixed in MHEA and MHEA+PREA carriers.

FIG. 2 shows an anti-decay effect of mixtures of active ingredient and carrier prepared by the company Granula Oy.

FIG. 3 shows an effect of the extraction schedules on the anti-decay properties of wood material.

FIG. 4 shows an anti-mildew effect of commercial and new active ingredients when mixed in MHEA and MHEA+PREA carriers.

FIG. 5 shows an anti-mildew effect of the mixtures of active ingredient and carrier produced by the company Granula Oy.

FIG. 6 shows an effect of the extraction schedules on the anti-decay properties of wood material.

DETAILED DESCRIPTION OF THE DRAWINGS

In the method for treating wood in accordance with the invention, the organic ammonium carboxylate of formula (1) is preferably in the form of an aqueous solution. The aqueous solution preferably has a concentration of e.g. 5-95% by weight and typically 15-45% by weight of total composition consisting ammonium carboxylate, organic active ingredient and possible water, additives and surfactants.

It has now been found, that the organic ammonium carboxylate of ammonium carboxylate of formula (1) is particularly suitable for transferring a wood preservative active ingredient into the wood that contains chelating agent(s) which provides wood properties against termites. Said active ingredient is preferably a mixture or a reaction product of an organic active ingredient salt and an organic active ingredient acid.

On the other hand, the invention is bases on the fact, that both polar poles of the formula (1) i.e. the ammonium cation and the carboxylic anion are readily adsorbed and absorbed to the treated wooden material. The small molecular size of the both polar molecules, the low surface tension and the special feature of both polar molecules to fasten in the hydrofobic and hydrofilic materials, components and molecules of the wood makes the organic ammonium carboxylate extremely effective in the use of wood treatment. The wooden material can be easily treated by the organic carboxylate and the organic carboxylate will stay inside the wooden material without leaching out.

When wood is treated with a solution comprising organic ammonium carboxylate of formula (1) and chelating agent(s) containing active ingredient wood material becomes more resistant to invertebrates and additionally can get better properties against fire (fire protection). The resistance against target invertebrates especially against insects such as ants and termites is based on repellent effect of chelating agents against said target invertebrate.

Wood can be treated in sufficiently large amounts with solution containing mentioned chelating agents and these chelating agents are not toxic for harmless invertebrates especially for harmless insects since their effect is based on their repelling effect on insects.

By using mentioned chelating agents which repels insects, in wood preservative solutions one can achieve additionally an unexpected advantage, since the use of chelating agents improves also the fire-protective properties of wood material.

Since the organic ammonium carboxylate of formula (1) is well absorbed into wood, it can, in another embodiment, be used as a further carrier of other active ingredients, such as active ingredients protecting the wood from micro-organisms.

Since the organic ammonium carboxylate of formula (1) is well absorbed into wood, it can, in another embodiment, be used as a carrier of other kind of active ingredients, such as active ingredients protecting the wood from micro-organisms.

The carrier then dissolves the active ingredient, transfers it in large amounts into the wood, and retains it in the wood.

Consequently, the quality and quantity of the ammonium carboxylate under consideration can be selected so that it transfers the wood-preservative agent to the wood.

It has been found that the organic ammonium carboxylate of formula (1) is particularly suitable for transferring wood preservative into wood comprising also a microbicide wood preservative. Microbicide wood preservative is preferable a mixture or a reaction product of an organic active ingredient salt and an organic active ingredient acid.

The microbicide organic active ingredient salt component of the active ingredient is preferably selected from the group comprising alkali metal, earth alkali metal and ammonium salts of aromatic acids, alkali metal, earth alkali metal and ammonium salts of aliphatic and aromatic sulphonic acids and acid salts of amines. Particularly advantageous organic active ingredient salts comprise sodium benzoate, sodium alkyl benzene sulphonate, cetyl pyridinium chloride and a salt of formic acid and ethanolamine. The latter also acts as a well absorbable organic ammonium carboxylate according to formula (1).

The organic active ingredient acid component of the active ingredient used for protecting wood from micro-organisms is preferably selected from the group comprising aromatic carboxylic and sulphonic acids, fatty acids, organic hydroxylic acids and their oligomers and chelating acids. Preferred substances comprise benzoic acid, $C_6$-$C_{20}$ fatty acid, preferably $C_{12}$-$C_{18}$ fatty acid such as stearic acid, and ethyl-enediamine-tetraacetic acid (EDTA). A mixture of benzoic acid and a $C_{12}$-$C_{18}$ fatty acid such as stearic acid is a particularly advantageous organic active ingredient component.

An advantageous combination of organic active ingredient acid and organic ingredient salt/ammonium carboxylate is EDTA+salt of ethanolamine together with formic acid and/or propionic acid.

The organic ammonium carboxylates according to formula (1) of the invention also serve for transferring other types of wood preservatives into wood, such as acidic copper chromate, ammoniacal copper zinc arsenate, chromate-containing copper arsenate, ammoniacal copper quaternary salt, copper bis(dimethyldithiocarbamate), ammoniacal copper citrate, copper azol-A and borate compound. Other applicable commercial wood preservatives (fungicides, insecticides, termicides etc.) comprise the active ingredients used in the brands Preventol® and K-Othrine®. Examples of these are Preventol®A8 (Tebucanazole), Preventol®MP 100 (IPBC), Preventol® HS11-N(Pyrethroide) and K-Othrine® 100 (Deltametrin). Examples of non-metallic wood preservatives which can be transferred into wood by mentioned ammonium carboxylate carrier are botulin and benzalkonium chloride (alkylbenzyldimethylammonium chlorides of various alkyl chain lengths) and polyhexamethyleneguanidine (PHMG) that is a particularly advantageous bioside because it acts as environmentally safe biocide. Further, the drying properties of PHMG are very good which speeds up the treating process.

When the ammonium carboxylates of formula (1) are used to transfer the copper compounds used as active ingredients mentioned above into the wood material, a mixture of two phases is produced as the ammonium carboxylates and the copper compounds react, because these copper compounds are water-insoluble. The first phase then contains an insoluble copper compound and the second phase contains an ammonium carboxylate complex or ionised ammonium carboxylate. The invention does not relate to a method for transferring merely a reaction product of ammonium carboxylate and copper compound into wood.

However, if the wood preservative contains copper compounds, borate, chromate or other metal compounds, the concentration of these metal compounds is kept relatively low. A suitable range is about 1-1.5 wt-% from the total weight of the composition (ammonium carboxylate of formula (I) and wood preservative). The concentration of metal compounds is kept sufficiently low for not to disturb function of polar poles of ammonium cation and carboxylic anion in ammonium carboxylate of formula (1). Since the purpose is to transfer wood preservative into wood and keep it there, metal containing preservatives will be transferred into wood so that there are always present free ammonioumcarboxylate and possible metal compounds are transferred in ionized state or as ammonium carboxylate-metal compounds-complexes.

In one embodiment of the invention, wood is treated with a view to protect it also from micro-organisms. In that case, the organic ammonium carboxylate of formula (1) may act as such as a wood preservative, with its quality and quantity selected so as to protect the wood from micro-organisms. In an aqueous solution, the weight ratio of organic ammonium carboxylate of formula (1) to water is then particularly in the range 1:20-20:1, preferably in the range 1:6-1:1. In this embodiment, the wood preservative contains typically 5-95% by weight of the agent of formula (1) preferably 15-45% by weight of the agent of formula (1).

Given the exceptionally good absorption into wood and retention in wood, one embodiment of the invention does not require environmentally hazardous copper and/or zinc to be included in the aqueous solution.

Some microbicide organic active ingredients mentioned above can be used in other purposes also. For example they can be used against termites (ethyl-enediaminetetraacetic acid (EDTA) or as surfactants (sodium alkyl benzene sulphonate and benzalkonium chloride).

In one embodiment, the ammonium carboxylate of formula (1) is used for transfer-ring other substances into the wood as well. Typical such substances comprise anti-oxidants, free-radical capturers, UV protective agents and wood extractives, such as tannins, described in WO 2009/101261 or WO 2009/101262 for Granula Ltd which WO-publications will be incorporated therein completely.

Wood is treated by a solution of ammonium carboxylate of formula (1) in combination with organic active ingredient as mentioned above in such a way that said solution is adsorbed and absorbed to the wood to be treated over the whole thickness thereof, or to a certain depth from the surface. Since various alternatives exists, the treatment may be carried out during processing of wood at suitable point, for instance during the final drying of the wood. The wood treatment solution of the invention may be heated and/or an elevated temperature may be used in the process, thus further improving the adsorption and absorption. The invention enables a convenient procedure for the treatment of wood materials in a cost effective manner, said procedure being easily incorporated into other common processes as one stage in the process line comprising successive steps for the treatment of wood product or articles for example first step using the pressure impregnation and the second step using spraying, painting or other surface treatment process by impregnating the wood with this agent or an aqueous solution of it under vacuum. The typical impregnating period is 1-120 minutes and the typical treatment temperature is 80-160° C. After impregnation the wood is usually rinsed.

The invention also relates to a wood preservative composition which provides protection against invertebrates specially against insects such as ants and termites. The composition contains organic ammonium carboxylate and an organic active ingredient containing a chelating agent that repels invertebrates. The organic ammonium carboxylate has the formula:

$$[NR^1R^2R^3R^4]^+{}_n[R^5(COO)_n]^{-n} \quad (1)$$

in which $R^1$, $R^2$ and $R^3$ have been selected from the group comprising hydrogen, substituted alkyls having 1-6 carbon atoms and unsubstituted alkyls having 1-6 carbon atoms, $R^4$ is a substituted alkyl having 1-6 carbon atoms or an unsubstituted alkyl having 1-6 carbon atoms, $R^5$ is hydrogen, a substituted hydrocarbyl having 1-6 carbon atoms or an unsubstituted hydrocarbyl having 1-6 carbon atoms, and n is an integer between 1-6. Active ingredient is selected from the group comprising an aminopolycarboxylic acid or a salt thereof, a hydroxy acid or a salt thereof or a phosphonate or a salt thereof or a mixture of chelating agents which belong to two of more groups thereof.

The wood preservative composition in accordance with the invention thus contains the same organic ammonium carboxylate of formula (1) and the same active ingredient that repels invertebrates and which are used in the wood preparation method described above. Hence the technical special features above relating to the organic ammonium carboxylate in combination with active ingredient and their composition also apply to the wood preservative composition of the invention. For this reason, only a number of crucial features of the composition will be repeated below.

In the organic ammonium carboxylate of formula (1) in the wood preservative composition, $R^5$ is preferably hydrogen, methyl or ethyl. $R^1$ is preferably hydrogen, $R^2$ and $R^3$ have preferably been selected from the group comprising hydrogen and 2-hydroxy ethyl, and $R^4$ is preferably 2-hydroxy ethyl.

The active ingredient which repels invertebrates is preferably an insects repelling active ingredient, more advantageously termite and/or ant repelling active ingredient. Preferably chelating agent binds iron and manganese ions and contains phosphorus (P) in the molecular structure. Typical chelating agents of this kind are 1-hydroxyethylidene,1,1-diphosphonic acid (HEDP), ethylenediaminetetramethyl-enephosphonic acid (EDTMP) or diethylenetriaiminepen-tamethylenephosphonic acid (DTPMP) or a mixture thereof.

Hence the organic ammonium carboxylate of formula (1) in the composition has preferably been selected from the group comprising a salt of formic acid and monoethanolamine, a salt of propionic acid and monoethanolamine or a mixture of these salts. The weight ratio of the mixture is preferably in the range 80:20-20:80.

The organic ammonium carboxylate of formula (1) is typically in the form of an aqueous solution having typically a concentration of 5-95% by weight from total composition comprising ammonium carboxylate of formula (1) and wood preservative composition containing chelating agent protecting wood from invertebrates, specially against insects such as termites and ants.

The chelating agent containing wood preservative solution against invertebrates is preferably in a form of an aqueous solution or dispersion having an active ingredient concentration of 0.01-95% by weight, more advantageously 0.01-45% by weigh and ammonium carboxylate concentration of 1-50% by weight. This kind of aqueous wood preservative solution can contain also surfactants and additives including other kind of active ingredients, viscosity modifiers, biocides, colouring agents, UV-protecting substances, agents modifying water repellency of composition, stability enhancers etc.

Surfactants are wetting agents that lower the surface tension of a liquid, allowing easier spreading, and lower the interfacial tension in between two liquids. A surfactant can be classified by the presence of formally charged groups in its head. A non-ionic surfactant has no charge groups in its head. The head of an ionic surfactant carries a net charge. If the charge is negative, the surfactant is more specifically called anionic; if the charge is positive, it is called cationic. If a surfactant contains a head with two oppositely charged groups, it is termed zwitterionic.

Instead of sodium alkyl benzene sulphonate can be used other surfactants also depending on the composition to be prepared. The use of tensides i.e. surfactants further improves the distribution and the penetration of the organic ammonium carboxylates of formula (1) and the wood preservative active ingredients and facilitates the dissolving of the film forming resins and emulsions based on fatty acids and/or polysaccharides i.e. prevents the phase separation in the readymade wood preservative.

Some commonly encountered surfactants of each type include anionic based on sulfate, sulfonate or carboxylate anions such as sodium dodecyl sulfate, ammonium lauryl sulfate, and other alkyl sulfate salts such as sodium laureth sulfate, alkyl benzene sulfonate or fatty acid salts; cationic based on quaternary ammonium cations such as cetylpyridinium chloride; nonionic such as alkyl polyglucosides, fatty alcohols including cetyl alcohol and oleyl alcohol.

The wood preservative composition according to invention can also include one or several microbisides as additives.

The organic ammonium carboxylate may act alone in the composition or together with another microbicide wood preservative compound as a microbicide, protecting wood additionally for microbes.

A microbicide wood preservative compound comprises preferably microbicide active ingredient that is a mixture or a reaction product of an organic active ingredient salt and an organic active ingredient acid. The organic active ingredient salt is typically sodium benzoate, sodium alkyl benzene sulphonate, cetyl pyridinium chloride, a salt of formic acid and ethanolamine, or a mixture of these. The organic active ingredient acid is typically benzoic acid, stearic acid, ethylenediamine-tetraacetic acid (EDTA) or a mixture of these.

From biocides we wish especially mention PHMG, which can be added preferably 0.001-5 wt-% to the wood preservative composition according to invention for enhance the protection against molds. Further, the drying properties of PHMG are very good which speeds up the treating process. Other polymeric guanidines or polymeric compounds can also be included into wood preservative composition.

Paint type resins such as fatty acids and/or polysaccharides may be added into wood preservative compositions of invention to further improve the water-repellency of wood material.

0.005-7 wt-% of tensides may be added to the wood preservative compositions to further improve stability thereof or to further facilitate adsorption and absorption of a wood preservative composition into wood.

The invention also relates to the use of the composition described above for preparing wood by impregnating the wood with this composition. It has also been surprisingly found that the ammonium carboxylate of the invention can be used either as such or together with known anti-corrosive agents for making wood corrosion-free, less corrosive or anti-corrosive. After preparation, the wood will prevent or reduce corrosion of metal bodies such as nails, screws or the like getting into contact with the wood.

The inventors has also found that the ammonium carboxylate of formula (1)

in which $R^1$, $R^2$ and $R^3$ have been selected from the group comprising hydrogen, substituted alkyls having 1-6 carbon atoms and unsubstituted alkyls having 1-6 carbon atoms, $R^4$ is a substituted alkyl having 1-6 carbon atoms or an unsubstituted alkyl having 1-6 carbon atoms, $R^5$ is hydrogen, a substituted hydrocarbyl having 1-6 carbon atoms or an unsubstituted hydrocarbyl having 1-6 carbon atoms, and n is an integer between 1-6 as such has invertebrate repelling properties. Invertebrate may be, for example a snail, worm or an insect. Specifically insect is a termite.

Depending on the application, ammonium carboxylate can be as a solid form or as a solution. Preferably ammonium carboxylate of formula (1) is used as a solution for treating wood material. Ammonium carboxylate treated wood material will then repel invertebrates, especially termites. The preferable structure and properties of ammonium ion $[NR^1R^2R^3R^4]^+_n$ and acid ion $[R^5(COO)_n]^{-n}$ in formula (1) has been discussed extensively above and therefore it is not our intention to repeat them in this connection.

Wood is treated by a solution of ammonium carboxylate of formula (1) in such a way that said solution is adsorbed and absorbed to the wood to be treated over the whole thickness thereof, or to a certain depth from the surface. The absorbing and adsorbing properties of ammonium carboxylate and also the general methods for preparing ammonium carboxylate solutions has discussed extensively above. Under the heading "Examples" we will give thereinafter some established methods for impregnating, spraying and painting wood material with solutions which is also applicable when used ammonium carboxylate containing solutions as such.

If ammonium carboxylate of formula (1) is used as a solution it is prepared as described above that is, by mixing an ammonium cation source and a carboxyl anion source in the desired molar ratio, either without a medium or by using an appropriate solvent such as water as a medium.

When ammonium carboxylate of formula (1) is used as a solid it is preferably a mixture of salt comprising a suitable molar ratio of salt of an ammonium component present in formula (1) mixed with suitable amount of moles of salt of an acid component present in formula (1).

The invertebrate repelling properties of ammonium carboxylate of formula (1) can be enhanced by using a mixture of liquid or water-soluble organic ammonium carboxylate and an active ingredient comprising chelating agents mentioned above.

In some instances the ammonium carboxylate of formula (I) may be used for repelling small vertebrates such as mouse and rat, bird and other pests.

EXAMPLES

A number of examples are given below with the sole purpose of illuminating the invention.
Compositions A typical aqueous solution for termite protection of food contains said wood preservative solution 0.01-10% by weight (for example phosphonate based HEDP) and the ammonium carboxylate of formula (1) and 1-45% by weight of chelative agent containing wood preservative active ingredient, the remainder being substantially water, additives and surfactants.

A typical aqueous solution for fire protection (and termites) contains said wood preservative solution (for example phosphonate based HEDP) 5-35% by weight and the ammonium carboxylate of formula (1) 1-30% by weight of chelative agent containing wood preservative active ingredient, the remainder being substantially water, additives and surfactants.

Preferably the chelating agent according to the invention is a chelating agent being able to bind iron and manganese ions and that contain phosphorus (P) in the molecular structure such as HEDP.

Example of a wood-protecting composition against insects especially against termites and ants.
Composition 1
Composition 1 is primarily targeted as repellant against insects, especially against termites
30 wt-% monoethanolammonium formiate (43 wt-% formic acid and 57 wt-% monoethanolamine)
8.33 wt-% Cublen KT600 (60 wt-% HEDP)
0.5 wt-% PHMG 20 (20 wt-% PHMG)
1 wt-% ionic tenside
rest is water
The composition of example 1 was well absorbed and adsorbed into wood and has excellent fixation into wood material.

For example of a composition which protects wood against fire and is also useful against insects especially against termites and ants
Composition 2
Composition 2 is intended primarily for protecting wood against fire but it has also repellant properties against insects such as termites
10 wt-% monoethanolammonium formiate (43 wt-% formic acid and 57 wt-% monoethanolamine)
49.2 wt % Cublen KT 600 (29.5 wt-% HEDP)
20.6 wt-% ammonia water (24.5 wt %) i.e. ammonia (100%)
3.6 wt-% ionic tenside
rest is water
The composition of example 2 was applied onto surface of plywood board made of spruce or birch. The composition was absorbed well into wood, about 250 g/m2 when applied once. Treated wood material showed excellent fire-protecting properties in a test according to standard EN5660.

The composition of example 2 was well absorbed and adsorbed into wood and has excellent fixation into wood material.

The compositions 1 and 2 can be used for impregnating, painting or spraying wood as described below.

Depending on the specific application and wood treating method the compositions according to invention can be modified very extensively as to their ammonium carboxylate and chelating agent content compared to those prepared in example 1 or 2. For example, if one uses composition according to example 2 and impregnates wood with this composition, it may be possible to lower then amount of chelating agent to about 1/20 from concentration shown in example 1 or 2.

The chelating agent 1-hydroxyethylidene,1,1-diphosphonic acid (HEDP) used in compositions 1 and 2 can be replaced by other phosphor containing chelating agents such as ethylenediaminetetramethylenephosphonic acid (EDTMP) or diethylenetriaiminepentamethylenephosphonic acid (DTPMP).

In the following are given exemplary microbiside active ingredients which can be also used in compositions and solutions containing above mentioned chelating agents which repels invertebrates. The ammonium carboxylate carriers mentioned in connection of those microbicide active ingredients may also be used when preparing above mentioned chelating agents which repels invertebrates.
Microbicide Studies
Objective
Studies are made in order to determine the microbicide effect of the system combining an ammonium carboxylate carrier and an active ingredient of the invention against micro-organisms that damage wood (mildews and blue stain and rot fungus).

1. Materials and Methods 1.1 Ammonium Carboxylate Carriers

Two ammonium carboxylate carrier mixtures were selected for the tests, with the water-soluble mixtures selected as shown in the accompanying table (table 1). A White Spirit solvent was additionally used as a reference carrier.

TABLE 1

Ammonium carboxylate carriers selected for the tests.

| Ammonium carboxylate carrier | Proportion of total carrier, % |
|---|---|
| MHEA | 100 |
| MHEA/PHEA | 70/30 |

MH = formic acid (actually its anion, i.e. formiate)
EA = ethanolamine (actually its cation, i.e. ethanolammonium)
PH = propionic acid (actually its anion, i.e. propionate)

2.2 Active Ingredients and their Mixtures

The active ingredients under study consisted of the commercial and new solutions listed in the central column of the following tables (2 and 3). The right-hand column of the tables corresponds to the ammonium carboxylate solutions used in accordance with table 1.

TABLE 2

Active ingredient and carrier mixtures used in decay tests

| Example | Active ingredient and its concentration | Carrier and its concentration |
|---|---|---|
|  | Commercial active ingredient: |  |
| 1 | 5% of Tebuconazole | 30% of MHEA |
| 2 | 5% of Tebuconazole | 30% of MHEA/PHEA |
|  | New active ingredient: |  |
| 3 | 5% of benzoic acid | 30% of MHEA |
| 4 | 5% of benzoic acid | 30% of MHEA/PHEA |
| 5 | 5% of EDTA in acid form | 30% of MHEA |
| 6 | 5% of EDTA in acid form | 30% of MHEA/PHEA |
| 7 | 5% of CEBE 2 | 30% of MHEA |
| 8 | 5% of CEOS | 30% of MHEA |
| 9 | 5% of BHTEB | 30% of MHEA |
| 10 | 5% of BEPRE | 30% of MHEA |
| 11 | 5% of SBBW-30 | 100% of White Spirit |
| Comparisons: Untreated wood |  |  |
| 12 (ref.) Wood treated with carrier alone | — | — |
| 13 (ref.) | — | 30% of MHEA |
| 14 | — | 30% of MHEA/PREA |
| 15 (ref.) | — | 100% of White Spirit |

EDTA = ethylenediaminetetraacetic acid
CEBE2 = 43% of MHEA + 43% of cetyl pyridinium benzoate + 9% Preventol MP100 + 5% EDTA
CEOS = 13% of stearic acid + 33% of lactic acid-oligomer + 6% of cetyl pyridium chloride + 48% of MHEA
BHTEB = 5% of Preventol A8 + 5% of benzoic acid + 90% of MHEA
BEPRE 100 = 4% of Preventol MP100 + 92% of MHEA
SBBW-30 = 30% (25% of stearic acid + 12% benzoic acid + 65% of alkylbenzyldimethy-lammonium chlorides of various alkyl chain lengths) + 70% White Spirit
Preventol A8 = Tebuconazole
Preventol MP 100 = IBPC = 3-iodine-2-propynyl butyl carbonate

TABLE 3

Active ingredient mixtures used in mildew and blue stain tests

| Example | Active ingredient and its concentration | Carrier and its concentration |
|---|---|---|
|  | Commercial active ingredient |  |
| 16 | 5% of IBPC | 30% of MHEA |
| 17 | 5% of IBPC | 30% of MHEA/PREA |
|  | New active ingredient |  |
| 18 | 5% of benzoic acid | 30% of MHEA |
| 19 | 5% of benzoic acid | 30% of MHEA/PREA |
| 20 | 5% of EDTA in acid form | 30% of MHEA |
| 21 | 5% of EDTA in acid form | 30% of MHEA/PREA |
| 22 | 5% of SBB | 30% of MHEA |
| 23 | 5% of CEBE2 | 30% of MHEA |
| 24 | 5% of CEOS | 30% of MHEA |
| 25 | 5% of BHTEB | 30% of MHEA |
| 26 | 5% of BEPRE 100 | 30% of MHEA |
| 27 | 5% of SBBW-30 | 100% of White Spirit |
| Comparisons: Untreated wood |  |  |
| 28 (ref.) Wood treated with carrier alone | — | — |
| 29 (ref.) | — | 30% of MHEA |
| 30 | — | 30% of MHEA/PREA |
| 31 (ref.) | — | 100% of White Spirit |

IBPC = 3-iodine-2-propynylbutylcarbonate 2.3 Extraction Tests of the Wood Material Oven-dry pine surface samples (15×15×5 mm) were extracted under five different extraction schedules (schedules 1-5). Unprocessed (unextracted) wood samples were used as reference material for the extracted wood material.

Extraction Schedule 1, Water Extraction

The wood samples were impregnated (vacuum impregnated) with water before extraction. The water-impregnated samples were extracted in an autoclave for 20 minutes at a temperature of 121° C.

Extraction Schedule 2, MHEA1

Wood samples were impregnated (vacuum impregnation) with a 50% MHEA carrier and the impregnated samples were extracted in an autoclave for 20 minutes at a temperature of 121° C. Then the samples were rinsed with cold water until the rinsing water was limpid (at least 3-4 rinses, one water rinse=in water over night under press).

Extraction Schedule 3, MHEA2

Wood samples were impregnated (vacuum impregnation) with a 50% MHEA carrier and the impregnated samples were extracted in an autoclave for 20 minutes at a temperature of 121° C. Then the samples were rinsed with cold water under press over night (one rinse).

Extraction Schedule 4, Solvent Extraction

Wood samples were extracted with acetone in a Soxhlet apparatus for 4 hours. After this the samples were further extracted with distilled water in a Soxhlet apparatus for 4 hours. The samples were not dried between the extractions.

Extraction Schedule 5, Solvent-MHEA-Extraction

Wood samples were extracted with acetone in a Soxhlet apparatus for 4 hours. Then the samples were further extracted with distilled water in a Soxhlet apparatus for 4 hours. The samples were not dried between the extractions. After the water extraction, the samples were air dried and impregnated (vacuum impregnation) with a 50% MHEA carrier. After they had been impregnated, the samples were rinsed with water under press over night.

2.4. Biological Effectiveness of Mixtures of Active Ingredient and Ancat and Extracted Wood 2.4.1 Decay Tests Small pine surface samples (15 mm×15 mm×5 mm) were vacuum impregnated with the active ingredient carrier mixture under study (table 2). Untreated samples and samples treated merely with ancat carriers or a White Spirit solvent were used as a reference. The brown-rot fungus *Coniophora-puteana*, BAM Ebw was selected as the test fungus. The fungus strain is derived from the strain collections of VTT Technical Research Centre of Finland, Building, Built Environment.

The amounts of mixtures of active ingredient-carrier absorbed into the samples (retention $kg/m^3$) were determined by calculatory means and dry basis weighing (dry weights of the samples before and after impregnation and rinsing). Part of the samples was rinsed with water before the decay tests were started. The rinsing was performed by impregnating the pieces with water and rinsing the samples under water for 4 days. The rinse water was renewed four times during the rinsing operation. The rinsing was performed under modified EN 84 standard. The amounts of active ingredient-carrier absorbed into the samples were determined also after the rinse.

The decay tests were conducted under accelerated and modified EN 113 standard. The reference samples and both unrinsed and rinsed test samples were allowed to decay over a period of 5 weeks. The effectiveness of the impregnation treatments was determined on the basis of the weight loss caused by the fungus.

2.4.2 Mildew and Blue Stain Tests

In mildew and blue stain tests, pine surface wood samples (25×50×5 mm) were vacuum impregnated with mixtures of active ingredient and carrier (table 3). The samples were not rinsed.

The anti-mildew and anti-blue stain effect of the mixtures of active ingredient and carrier and their references were examined in a laboratory by a suspending method. The test samples and the reference samples were suspended in random order in exposure chambers. The relative humidity in the chambers was regulated by means of water in the range 95–100% at a test temperature of 20° C. (+/−2° C.).

Blue stain and mildew fungus suspensions were injected into the test boxes before the test was started. The mildew suspension contained three mildew species that thrive in wood: *Aspergillus versicolor* (E1), *Gladosporium sphaerospermum* (R7) and *Penicillium* sp. (1017). The blue stain suspension consisted of the following species: *Aureobasidium pullulans* (T1), *Sclerophoma entoxylina* (Z17) and *Ceratocystispilifera* (Z11). The fungus strains are derived from the strain collections of VTT Technical Research Centre of Finland, Building, Built Environment. The moulding of the test samples was monitored visually at the end of 2, 4, 6, 8 and 10 weeks from the start of the test on a scale 0–5.

0=no growth
s1=marks of starting growth (microscopically observable)
2=1-10% of the area covered by microbial growth (microscopically observable)
3=10-30% of the area covered by microbial growth (visually observable)
4=30-70% of the area covered by microbial growth (visually observable)
5=100% of the area covered by microbial growth (visually observable)

3. Results 3.1 Anti-Decay Effect of the Mixtures of Active Ingredient and Carrier and the Extraction Schedules The cellar fungus (*C. puteana*) is a brown-rot fungus that causes weight loss and reduces the strength of wood material. The metabolism of brown-rot fungi utilises the hydrocarbon structural components of wood (hemi-cellulose and cellulose) and also modifies the lignin structure. If brown rot proceeds over a long period, there will remain only brittle lignin, which decomposes into dust even under light stress.

The results of the decay tests are illustrated in FIGS. 1-3. The results indicate that all of the mixtures of active ingredient and carrier and ancat carriers under study, when not rinsed, prevented alone the decay caused by *C. puteana* in an accelerated decay test. In all the cases, the weight loss of the samples was smaller than the weight loss set as the preservative effect limit under the EN 113 standard ($\leq 3\%$).

A weight loss of less than 3% was achieved in the rinsed samples when the preservative contained tebuconazole-MHEA, tebuconazole-MHEA+PREA, CEBE2–MHEA, CEOS–MHEA or BHTEB–MHEA. A weight loss limit of almost 3% was achieved with rinsed samples containing benzoic acid-MHEA+PREA (4.2% by weight loss) or EDTA–MHEA+PREA in acid form (5.2% weight loss). The rinse clearly reduced the anti-decay effect of benzoic acid-MHEA (7.3% by weight loss) and of EDTA–MHEA in acid form (12.7% weight loss).

When unrinsed, both the ancat carriers prevented efficiently the weight loss caused by rot fungus in the test samples. The effectiveness of MHEA+PREA decreased after rinsing, and a weight loss of 9% was stated in the test samples. WhiteSpirit did not prevent the weight loss caused by rot fungus. By contrast, a mixture of SBBW30 and WhiteSpirit proved to have a high anti-decay effect both when rinsed and not rinsed.

The objective of the extraction tests was to determine whether removal of e.g. soluble sugars or structural components soluble in the carrier increases the decay resistance of wood. Ancat carriers have proved (cf. the results of the extraction tests) to extract hydrocarbons and particularly xylane of hemi-cellulose from the wood material. The results of the decay tests indicated that water extraction (extraction schedule 1), MHEA1 (extraction schedule 2) and solvent extraction (extraction schedule 4) did not increase the decay resistance of extracted wood material (weight losses>30%). By contrast, in samples treated under extraction schedules 3 (MHEA2) and 5 (solvent-MHEA extraction) the weight loss caused by rot fungus was under the 3% limit prescribed by the standard.

FIG. 3. Effect of the Extraction Schedules on the Anti-Decay Properties of Wood Material.

Table 4 presents the active ingredient-carrier contents absorbed into the samples during impregnation. The contents were relatively high, with variations in the range 190–240 $kg/m^3$. Rinsing had no notable effect on the absorption.

TABLE 4

Active ingredient contents in the test samples after impregnation and rinsing.

| Example | Mixture active ingredient-carrier | Retention kg/m³ | |
|---|---|---|---|
| | | Not rinsed | Rinsed |
| 13 | MHEA | 201 | 194 |
| 14 | MHEA + PREA | 182 | 182 |
| 3 | Benzoic acid-MHEA | 213 | 225 |
| 4 | Benzoic acid-MHEA/PREA | 204 | 214 |
| 5 | EDTA-MHEA in acid form | 222 | 217 |
| 6 | EDTA-MHEA/PREA in acid form | 209 | 203 |
| 1 | Tebuconazole-MHEA | 222 | 222 |
| 2 | Tebuconazole-MHEA/PREA | 194 | 193 |
| 7 | CEBE2-MHEA | 205 | 208 |

TABLE 4-continued

Active ingredient contents in the test samples after impregnation and rinsing.

| Example | Mixture active ingredient-carrier | Retention kg/m³ | |
|---|---|---|---|
| | | Not rinsed | Rinsed |
| 8 | CEOS-MHEA | 231 | 233 |
| 9 | BHTEB-MHEA | 235 | 235 |
| 10 | BEPRE100-MHEA | 236 | 228 |

3.2 Anti-Mildew and Anti-Blue Stain Effect of Mixtures of Active Ingredient/Carrier and Extraction Schedules Blue stain fungi penetrate into the wood material structure, and by staining the wood, they entail discolouration and alter the moisture behaviour of the material (the material will have higher water absorption). The metabolism of blue stain fungi utilises mainly soluble nutrients, and they do not usually produce weight losses or decrease the strength of the wood. By contrast, mildew fungi grow only on the surface of the wood material. Mildews do not penetrate into the material structure and thus do not cause weight losses or decreased strength. Mildews live on the soluble nutrient present on the material surface. The damages caused by mildews relate to discolouration and malodour and possible health hazards.

The blue stain tests did not yield any results. Blue stain was not observed in one single treated or untreated sample during an exposure period of 10 weeks. In the case of the untreated reference, this zero result may also be partly due to excessive moisture of the samples, which in turn is caused by the hygroscopicity of the mixtures of active ingredient and carrier, to the susceptibility of blue stain fungi to the compounds under study and/or to transfer of the active ingredients also to the untreated reference sample, owing to the high transfer potential of the carrier.

The results of the mildew tests are shown in FIGS. 4–6. The corresponding examples are given in table 3. Mildew growth was prevented completely in an exposure test of 10 weeks when the samples were treated with the following mixtures of active ingredient and carrier: benzoic acid-MHEA– (example 18), benzoic acid-MHEA+PREA (example 19), EDTA–MHEA in acid form (example 20), EDTA–MHEA–PREA in acid form (example 21), SBB–MHEA (example 22), CEBE2-MHEA (example 23) and BEPRE100–MHEA (example 26) and SBBW30-WhiteSpirit. In untreated control samples and test samples treated with WhiteSpirit, moulding reached the mildew index 5 (100% of the sample surface was covered by mildew growth) after 6 weeks' exposure. Moderate mildew growth was observed in the two samples treated with ancat carriers. The mildew index reached the value 2 during the exposure (mildew growth not yet visible). Moderate mildew growth (mildew index 2) was also observed in test samples treated with active ingredient mixtures of CEBE2-MHEA (example 23) and CEOS–MHEA (example 24).

The objective of the extraction tests was to determine whether the removal of e.g. soluble sugars or structural components soluble in the carrier increases the mildew resistance of the wood. The results of the mildew tests show that water extraction (extraction schedule 1), MHEA2 (extraction schedule 3) and solvent extraction (extraction schedule 4) did not increase the mildew resistance of the extracted wood material, with a mildew index variation between 3 and 5 in these cases (visible and abundant growth). On the contrary, moulding was moderate in samples treated under extraction schedules 2 and 5 (MHEAI and solvent-MHEA extraction) (mildew index 1 or less).

4. Conclusions of Mibrobicide Studies

The mixtures of active ingredient and carrier were observed to have a distinct preventive potential both with respect to decay and to mildew formation. The decay tests determined the anti-decay effect of MH/EA and MH/EA+PR/EA carriers and of active ingredients mixed in these (benzoic acid, EDTA in acid form, tebuconazole, CEBE2, BHTEB, BEPRE 100-MHEA, CEOS). The decay tests also determined the effect of SBB dissolved in a WhiteSpirit solvent. Wood samples extracted under five different extraction schedules were also included in the decay tests.

The mixtures of active ingredient and carrier efficiently prevented decay caused by *C. puteana* in an accelerated decay test. The test results indicated that the mixtures of active ingredient and carrier efficiently prevented weight loss caused by rot fungus in the treated wood samples also after rinsing. The most efficient active ingredient mixtures with the highest anti-decay potential occurred among the formulations produced by the company Granula Oy.

The mildew and blue stain tests, in turn, determined the anti-mildew effect and anti-blue stain effect of MH/EA and MH/EA+PR/EA carriers and of active ingredients mixed in these carriers (benzoic acid, EDTA, IBPC, SBB, CEBE2, CEOS, BHTEB, BEPRE 100-MHEA in acid form) and SBB dissolved in a WhiteSpirit solvent. The test results showed that the mixtures of active ingredient and carrier actively prevented mildew growth on the surface of the treated wood samples during an exposure period of 10 weeks. No blue staining was observed. This result may be due to excessive moisture of the samples, which in turn was caused by the hydroscopicity of the mixtures of active ingredient and carrier, to the susceptibility of blue stain fungi to the compounds under study and/or to transfer of active ingredients also to the untreated reference sample, owing to the high transfer potential of the carrier.

The effect of extraction of the soluble and structural components of wood material on decay and mildew formation was determined by treating the wood material under five different extraction schedules. Water and solvent extractions had no effect on the decay and mildew resistance of the wood material. Decay caused by *C. puteana* was inhibited in the cases where the wood material contained a carrier after the extraction.

In the following, practical examples will be given of methods how compositions according to invention can be used for the treatment of wood and how the treatment can be integrated in a wood material processing line in mills for wood processing.

1) Pressure Impregnation

A conventional method for entering great amounts of impregnation substance in wood, and thereby providing the most effective treatment by means of different steps (negative pressure and overpressure, elevated temperature). By this method, the best penetrability of compositions is obtained, and the wood can normally be impregnated to the core. The composition according to the invention has a very good penetrability, wherein it is possible to reduce the negative pressures/overpressures used in conventional CCA impregnation and thereby to improve the cost-effectiveness of the process. Also, a tighter-grained type of wood, such as spruce, can be pressure impregnated with the composition according to the invention, which has not been possible with conventionally used substances.

2) Immersion Impregnation

The penetrability of the composition according to the invention is good, and in some cases, mere immersion impregnation is also possible. This method is simple but it requires separate immersion basins and is carried out in batch processes, like the pressure impregnation.

3) Spraying

The composition according to the invention can be sprayed onto the surface of wood, for example, in connection with the planning of sawn timber. In this way, preservation against microorganisms can be achieved during storage and delivery before a surface treatment (painting etc.) later on.

4) Painting or Other Surface Treatment Line

The composition according to the invention may also be added into the wood in connection with a painting or another surface treatment line. From a paint dosing tank, a wooden board can be impregnated with the solution under overpressure or negative pressure through a separate painting unit. Depending on the pressure and the speed of the line, relatively good penetrability and thereby a reasonable resistance to weather and fire can be achieved by this method.

5) Drying of the Wood and the Control of Final Moisture Content

In the processing of timber in sawmills, it is more and more important that the final moisture content of the wood is suitable to prevent cracking and dimensional changes, as well as to prevent too good a substrate from forming for biological life. In connection with the drying, the tree often dries to a moisture content that is lower than desired. At the end, the moisture content can be adjusted, for example, by a technique based on spraying with water. In this step, it is very easy to add the composition according to the invention into the wood, wherein it is possible to eliminate cracking and dimensional changes due to the drying of wood. Furthermore, this method can be used to improve the fire resistance and to provide at least a short-term preservation against micro-organisms.

In connection with the treatment methods according to points 1 to 4, however, it is important to dry the wood well (for example, at a temperature from 40 to 80 C), wherein the extra water absorbed in the wood during the process can be removed and the moisture content can be stabilized to a desired final level.

By the solution of the invention, it possible to facilitate the treatment of wood under winter conditions where the processing of frozen wood (for example, melting, impregnation, planning, painting, etc.) is problematic and constitutes an extra cost item.

Usually ammonium carboxylate of formula (1) as mentioned above is absorbed into wood by impregnating the wood with this agent or an aqueous solution of it under vacuum. The typical impregnating period is 1-120 minutes and the typical treatment temperature is 80-160° C. After impregnation the wood is usually rinsed.

The invention claimed is:

1. A method for treating wood, comprising bringing the wood into contact with a mixture of liquid or water-soluble organic ammonium carboxylate and an active ingredient which repels invertebrates, wherein the organic ammonium carboxylate has the formula (1):

  (1)

in which $R^1$, $R^2$ and $R^3$ are selected from the group consisting of hydrogen, substituted and unsubstituted alkyls containing 1-6 carbon atoms, $R^4$ is a substituted or unsubstituted alkyl containing 1-6 carbon atoms, $R^5$ is hydrogen, a substituted or unsubstituted hydrocarbon containing 1-6 carbon atoms and n is an integral 1-6 and wherein the wood-preservative active ingredient contains a chelating agent which repels invertebrate, and the chelating agent is selected from the group consisting of an aminopolycarboxylic acid or a salt thereof, a hydroxy acid or a salt thereof or a phosphonate or a salt thereof and a mixture of chelating agents which belong to two of more groups thereof.

2. The method as defined in claim 1, wherein the active ingredient containing chelating agent is a mixture or reaction product of an organic active ingredient salt and an organic active ingredient acid.

3. The method as defined in claim 1, wherein the chelating agent is selected from the group consisting of ethylenediaminetetra-acetic acid (EDTA), nitrolotriacetic acid (NTA), n-hydroxyethyl-ethylenediaininetriacetic acid (HEDTA), diethylenetriaminepentaacetic acid (DTPA), ethylediamine-di-o-hydroxyphenylacetic acid (EDDHDA), diethanolglycine (DEG), ethanoldiglycine (EDG) or salt thereof or 1-hydroxyethylidene,1,1-diphosphonic acid (HEDP), ethylenediaminetetramethylenephosphonic acid (EDTMP), diethylenetriaiminepentamethylenephosphonic acid (DTPMP) or salt thereof and a mixture thereof.

4. The method as defined in claim 3, wherein the chelating agent is a phosphor containing chelating agent selected from the group consisting of 1-hydroxyethylidene,1,1-diphosphonic acid (HEDP), ethylenediaminetetramethylenephosphonic acid (EDTMP), diethylenetriaiminepentamethylenephosphonic acid (DTPMP) or salt thereof and a mixture thereof.

5. The method as defined in claim 1, wherein $R^5$ is hydrogen, a substituted or unsubstituted alkyl containing 1-6 carbon atoms and n is 1 or 2.

6. The method as defined in claim 5, wherein $R^5$ is a substituted or unsubstituted alkyl containing 1-4 carbon atoms, and n is 1.

7. A method as defined in claim 5, wherein $R^5$ is hydrogen, methyl or ethyl.

8. The method as defined in claim 1, wherein $R^1$ is hydrogen, $R^2$ and $R^3$ are selected from the group comprising hydrogen and $C_1$-$C_6$ alkyls substituted with a hydroxyl group, and $R^4$ is a $C_1$-$C_6$-alkyl substituted with a hydroxyl group.

9. A method as defined in claim 8, wherein $R^1$ is hydrogen, $R^2$ and $R^3$ are selected from the group consisting of hydrogen and ethyl substituted with a hydroxyl group, and $R^4$ is an ethyl substituted with a hydroxyl group.

10. The method as defined in claim 1, wherein the organic ammonium carboxylate of formula (1) is a salt of formic acid and monoethanolamine or a salt of propionic acid and monoethanolamine.

11. The method as defined in claim 1, wherein the organic ammonium carboxylate of formula (1) is a mixture of a salt of formic acid and monoethanolamine and a salt of propionic acid and monoethanolamine.

12. The method as defined in claim 1, wherein the organic ammonium carboxylate of formula (1) is selected with a quality and quantity such that it protects wood against microorganisms.

13. The method as defined in claim 1, wherein the organic ammonium carboxylate of formula (1) is selected with a quality and quantity such that it transfers a microbicide active ingredient into the wood.

14. The method as defined in claim 1, wherein the wood is treated by impregnating, spraying or painting with liquid or water-soluble organic ammonium carboxylate and any active ingredient.

15. The method as defined in claim 14, wherein the wood is dried before it is treated by the method mentioned in claim 14.

16. A wood preservative composition comprising organic ammonium carboxylate and organic active ingredient which repels invertebrates, wherein the organic ammonium carboxylate has the formula (1):

$$[NR^1R^2R^3R^4]^+{}_n[R^5(COO)_n]^{-n} \quad (1)$$

in which $R^1$, $R^2$ and $R^3$ are selected from the group consisting of hydrogen, substituted and unsubstituted alkyls containing 1-6 carbon atoms, $R^4$ is a substituted or unsubstituted alkyl containing 1-6 carbon atoms, $R^5$ is hydrogen, a substituted or unsubstituted hydrocarbon containing 1-6 carbon atoms and n is an integral 1-6, and wherein the composition comprise additionally an active ingredient which contains a chelating agent that repels invertebrates, and the active ingredient is selected from the group consisting of an aminopolycarboxylic acid or a salt thereof, a hydroxy acid or a salt thereof or a phosphonate or a salt thereof and a mixture of chelating agents which belong to two of more groups thereof.

17. The composition as defined in claim 16, wherein the active ingredient containing chelating agent is a mixture or reaction product of an organic active ingredient salt and an organic active ingredient acid.

18. The composition as defined in claim 17, wherein the chelating agent is selected from the group consisting of ethylenediaminetetra-acetic acid (EDTA), nitrolotriacetic acid (NTA), n-hydroxyethyl-ethylenediaininetriacetic acid (HEDTA), diethylenetriaminepentaacetic acid (DTPA), ethylediamine-di-o-hydroxyphenylacetic acid (EDDHDA), diethanolglycine (DEG), ethanoldiglycine (EDG) or salt thereof or 1-hydroxyethylidene,1,1-diphosphonic acid (HEDP), ethylenediaminetetramethylenephosphonic acid (EDTMP), diethylenetriaiminepentamethylenephosphonic acid (DTPMP) or salt thereof and a mixture thereof.

19. The composition as defined in claim 16, wherein the chelating agent is a phosphor containing chelating agent selected from the group consisting of 1-hydroxyethylidene, 1,1-diphosphonic acid (HEDP), ethylenediaminetetramethylenephosphonic acid (EDTMP), diethylenetriaiminepentamethylenephosphonic acid (DTPMP) or salt thereof and a mixture thereof.

20. The composition as defined in claim 16, wherein chelating agent repels termites and ants.

21. The composition as defined in claim 16, wherein $R^5$ is hydrogen, a substituted or unsubstituted alkyl containing 1-6 carbon atoms, and n is 1 or 2.

22. The composition as defined in claim 21, wherein $R^5$ is hydrogen, methyl or ethyl.

23. The composition as defined in claim 16, wherein $R^1$ is hydrogen, $R^2$ and $R^3$ are selected from the group consisting of hydrogen and $C_1$-$C_6$ alkyls substituted with a hydroxyl group, and $R^4$ is a $C_1$-$C_6$-alkyl substituted with a hydroxyl group.

24. The composition as defined in claim 23, wherein $R^1$ is hydrogen, $R^2$ and $R^3$ are selected from the group consisting of hydrogen and ethyl substituted with a hydroxyl group, and $R^4$ is an ethyl substituted with a hydroxyl group.

25. The composition as defined in claim 16, wherein the organic ammonium carboxylate of formula (1) is a salt of formic acid and monoethanolamine or a salt of propionic acid and monoethanolamine or mixture thereof.

26. The composition as defined in claim 16, wherein the chelating agent intended against termites is in the form of an aqueous solution or dispersion having an active ingredient concentration of 0.01-95% by weight and ammonium carboxylate concentration of 1-50% by weight.

27. The composition as defined in claim 26 for protection of wood against termites, wherein the composition comprises phosphor based chelating agent 0.01-10% by weight, ammonium carboxylate of formula (1) 1-45% by weight the remainder being substantially water, additives and surfactants.

28. The composition as defined in claim 27 for protection of wood against fire, wherein the composition comprises phosphor based chelating agent 5-35% by weight, ammonium carboxylate of formula (1) 1-30% by weight the remainder being substantially water, additives and surfactants.

29. The composition as defined in claim 26, wherein the organic ammonium carboxylate of formula (1) is selected with a quality and quantity such that it protects the wood against micro-organisms by itself.

30. The composition as defined in claim 26, wherein the wood preservative composition further comprises surfactant(s) and/or additives including other kind of active ingredients than invertebrates repelling active ingredients.

31. The composition as defined in defined in claim 30, wherein the wood preservative composition further comprises microbicide active ingredient as an additive.

32. The composition as defined in claim 31, wherein the wood that microbicide active ingredient is a mixture or a reaction product of an organic active ingredient salt and an organic active ingredient acid.

33. The composition as defined in claim 32, wherein the organic active ingredient salt is selected from the group consisting of alkali metal, earth alkali metal and ammonium salts of aromatic acids, alkali metal, earth alkali metal and ammonium salts of aliphatic and aromatic sulphonic acids and acid salts of amines.

34. The composition as defined in claim 33, wherein the organic active ingredient salt is selected from the group consisting of sodium benzoate, sodium alkyl benzene sulphonate, cetyl pyridinium chloride and a salt of formic acid and ethanolamine.

35. The composition as defined in claim 31, wherein the microbicide active ingredient is selected from the group consisting of acidic copper chromate, ammoniacal copper zinc arsenate, chromate-containing copper arsenate, ammoniacal copper quaternary salt, copper bis(dimethyldithiocarbamate), ammoniacal copper citrate, copper azol-A and borate compound.

36. The composition as defined in claim 35, wherein the composition comprises about 0.01-1.5 wt % microbicide.

37. The composition as defined in claim 31, wherein the microbicide active ingredient is selected from the group consisting of botulin, benzalkonium chloride (alkylbenzyldimethylammonium chlorides of various alkyl chain lengths) and polyhexamethyleneguanidine (PHMG).

38. The composition as defined in claim 37, further comprising surfactants which are selected from the group consisting of anionic surfactants; cationic surfactants based on quaternary ammonium cations ide; nonionic surfactants; and fatty alcohols.

39. The composition as defined in claim 37, further comprising additives selected from group consisting of viscocity modifiers, anti-oxidants, free-radical capturers, UV protective agents and wood extractives.

40. A composition against invertebrates comprising organic ammonium carboxylate and invertebrates rebelling organic active ingredient wherein the organic ammonium carboxylate has the formula (1):

$$[NR^1R^2R^3R^4]^+{}_n[R^5(COO)_n]^{-n} \quad (1)$$

in which $R^1$, $R^2$ and $R^3$ are selected from the group consisting of hydrogen, substituted and unsubstituted alkyls containing 1-6 carbon atoms, $R^4$ is a substituted or unsubstituted alkyl containing 1-6 carbon atoms, $R^5$ is hydrogen, a substituted or unsubstituted hydrocarbon containing 1-6 carbon atoms and n is an integral 1-6, and wherein the composition comprises additionally an active ingredient containing a chelating agent that repels invertebrates, and the active ingredient is selected from the group consisting of an aminopolycarboxylic acid or a salt thereof, a hydroxy acid or a salt thereof or a phosphonate or a salt thereof and a mixture of chelating agents which belong to two of more groups thereof.

41. The composition as defined in claim 40, wherein the chelating agent is selected from the group consisting of ethylenediaminetetra-acetic acid (EDTA), nitrolotriacetic acid (NTA), n-hydroxyethyl-ethylenediaininetriacetic acid (HEDTA), diethylenetriaminepentaacetic acid (DTPA), ethylediamine-di-o-hydroxyphenylacetic acid (EDDHDA), diethanolglycine (DEG), ethanoldiglycine (EDG) or salt thereof or 1-hydroxyethylidene,1,1-diphosphonic acid (HEDP), ethylenediaminetetramethylenephosphonic acid (EDTMP), diethylenetriaminepentamethylenephosphonic acid (DTPMP) or salt thereof and a mixture thereof.

42. The composition as defined in claim 41, wherein the chelating agent is a phosphor containing chelating agent selected from the group consisting of 1-hydroxyethylidene, 1,1-diphosphonic acid (HEDP), ethylenediaminetetramethylenephosphonic acid (EDTMP), diethylenetriaminepentamethylenephosphonic acid (DTPMP) or salt thereof and a mixture thereof.

43. The composition as defined in claim 40, wherein $R^5$ is hydrogen, a substituted or unsubstituted alkyl containing 1-6 carbon atoms, and n is 1 or 2.

44. The composition as defined in claim 43, wherein $R^5$ is hydrogen, methyl or ethyl.

45. The composition as defined in claim 44, wherein $R^1$ is hydrogen, $R^2$ and $R^3$ are selected from the group consisting of hydrogen and $C_1$-$C_6$ alkyls substituted with a hydroxyl group, and $R^4$ is a $C_1$-$C_6$-alkyl substituted with a hydroxyl group.

46. The composition as defined in claim 45, wherein $R^1$ is hydrogen, $R^2$ and $R^3$ are selected from the group consisting of hydrogen and ethyl substituted with a hydroxyl group, and $R^4$ is an ethyl substituted with a hydroxyl group.

47. The composition as defined in claim 40, further comprising surfactants and additives selected from the group consisting of microbisides, anti-oxidants, free-radical capturers, UV protective agents and wood extractives.

48. A method for repelling an invertebrate comprising subjecting an invertebrate with an organic ammonium carboxylate of formula (1):

 (1)

in which $R^1$, $R^2$ and $R^3$ are selected from the group selected from the group consisting of hydrogen, substituted and unsubstituted alkyls containing 1-6 carbon atoms, $R^4$ is a substituted or unsubstituted alkyl containing 1-6 carbon atoms, $R^5$ is hydrogen, a substituted or unsubstituted hydrocarbon containing 1-6 carbon atoms and n is an integral 1-6.

49. The method as defined in claim 47, wherein $R^5$ is hydrogen, a substituted or unsubstituted alkyl containing 1-6 carbon atoms and n is 1 or 2.

50. The method as defined in claim 49, wherein $R^5$ is a substituted or unsubstituted alkyl containing 1-4 carbon atoms, and n is 1.

51. The method as defined in claim 48, wherein $R^5$ is hydrogen, methyl or ethyl.

52. The method as defined in claim 48, wherein $R^1$ is hydrogen, $R^2$ and $R^3$ are selected from the group consisting of hydrogen and $C_1$-$C_6$ alkyls substituted with a hydroxyl group, and $R^4$ is a $C_1$-$C_6$-alkyl substituted with a hydroxyl group.

53. The method as defined in claim 52, wherein $R^1$ is hydrogen, $R^2$ and $R^3$ are selected from the group comprising hydrogen and ethyl substituted with a hydroxyl group, and $R^4$ is an ethyl substituted with a hydroxyl group.

54. The method as defined in claim 48, wherein the organic ammonium carboxylate of formula (1) is a salt of formic acid and monoethanolamine or a salt of propionic acid and monoethanolamine.

55. The method as defined in claim 48, wherein the organic ammonium carboxylate of formula (1) is a mixture of a salt of formic acid and monoethanolamine and a salt of propionic acid and monoethanolamine.

56. The method as defined in claim 48, wherein the invertebrate is an insect, and the insect is subjected with organic ammonium carboxylate of formula (1) that is impregnated into wood by bringing wood into contact by a mixture of liquid or water-soluble organic ammonium carboxylate of formula (1).

57. The method as defined in claim 56, wherein the insect is a termite.

* * * * *